(12) United States Patent
Letzelter et al.

(10) Patent No.: US 10,301,578 B2
(45) Date of Patent: May 28, 2019

(54) AUTOMATIC DISHWASHING

(71) Applicant: The Procter & Gamble Company, Cincinnati, OH (US)

(72) Inventors: Nathalie Sophie Letzelter, Trimdon (GB); Rachel Elizabeth Martin, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/481,490

(22) Filed: Apr. 7, 2017

(65) Prior Publication Data

US 2017/0292094 A1 Oct. 12, 2017

(30) Foreign Application Priority Data

Apr. 8, 2016 (EP) .................................... 16164574

(51) Int. Cl.
| | | |
|---|---|---|
| *C11D 3/26* | (2006.01) | |
| *C11D 3/386* | (2006.01) | |
| *C11D 3/33* | (2006.01) | |
| *C11D 3/39* | (2006.01) | |
| *C11D 11/00* | (2006.01) | |
| *C11D 17/04* | (2006.01) | |

(52) U.S. Cl.
CPC ............. *C11D 3/386* (2013.01); *C11D 3/33* (2013.01); *C11D 3/3905* (2013.01); *C11D 11/0023* (2013.01); *C11D 17/042* (2013.01); *C12Y 302/01* (2013.01); *C12Y 304/00* (2013.01)

(58) Field of Classification Search
CPC .... C11D 3/33; C11D 17/0091; C11D 3/38609
USPC .................... 510/226, 221, 392, 220, 439
See application file for complete search history.

(56) References Cited

U.S. PATENT DOCUMENTS

| | | |
|---|---|---|
| 5,856,164 A | 1/1999 | Outtrup et al. |
| 6,093,562 A | 7/2000 | Bisgard-Frantzen et al. |
| 8,883,711 B2 | 11/2014 | Leonard et al. |
| 2008/0193999 A1 | 8/2008 | Andersen et al. |
| 2010/0041575 A1 | 2/2010 | Warkotsch et al. |
| 2010/0075885 A1* | 3/2010 | Brooker ............... C11D 3/1213 510/221 |
| 2010/0075886 A1* | 3/2010 | Brooker ............... C11D 3/1213 510/226 |
| 2011/0139182 A1* | 6/2011 | Lapham .................. C11D 1/66 134/18 |
| 2012/0067373 A1* | 3/2012 | Souter ..................... C11D 3/33 134/18 |
| 2012/0240961 A1* | 9/2012 | Denome ............. C11D 17/042 134/25.2 |
| 2014/0228271 A1 | 8/2014 | Eiting et al. |
| 2015/0087572 A1* | 3/2015 | Souter ..................... C11D 3/33 510/226 |
| 2016/0208198 A1* | 7/2016 | Souter ..................... C11D 3/33 |
| 2016/0222323 A1* | 8/2016 | Letzelter ............. C11D 3/2086 |
| 2016/0222325 A1* | 8/2016 | Letzelter ............. C11D 3/3761 |

FOREIGN PATENT DOCUMENTS

| | | |
|---|---|---|
| EP | 2 392 638 A1 | 12/2011 |
| WO | WO 94/22800 A1 | 10/1994 |
| WO | WO 96/23873 A1 | 8/1996 |
| WO | WO 99/23211 A1 | 5/1999 |
| WO | WO 00/37627 A1 | 6/2000 |
| WO | WO 00/60060 A2 | 10/2000 |
| WO | WO 2008/010925 A2 | 1/2008 |
| WO | WO 2009/092699 A1 | 7/2009 |
| WO | WO 2014/184280 A1 | 11/2014 |
| WO | WO 2016/041681 A1 | 3/2016 |

OTHER PUBLICATIONS

International Search Report; International Application No. PCT/US2017/024436; dated Jun. 21, 2017; 13 pages.

\* cited by examiner

*Primary Examiner* — Gregory E Webb
(74) *Attorney, Agent, or Firm* — John T. Dipre

(57) ABSTRACT

A method of cleaning a soiled dishware load in an automatic dishwashing machine including the step of subjecting the load to a wash liquor including at least 700 ppm of an aminocarboxylated complexing agent and wherein the liquor is free of phosphate and free of dispersant polymer.

10 Claims, No Drawings

AUTOMATIC DISHWASHING

FIELD OF THE INVENTION

The present invention relates to automatic dishwashing, in particular a method of automatic dishwashing using a wash liquor free of phosphate and free of dispersant polymer and comprising a high level of an aminocarboxylated complexing agent. The method provides good cleaning, prevention of spotting, provides good shine and presents a good environmental profile. The invention also relates to an automatic dishwashing composition and the use of the composition to prevent spotting in automatic dishwashing.

BACKGROUND OF THE INVENTION

The role of automatic dishwashing is twofold: to clean soiled dishware and to leave it shiny. Typically when water dries from surfaces water-marks, smears and/or spots are left behind. These water-marks may be due to the evaporation of water from the surface leaving behind deposits of minerals which were present as dissolved solids in the water, for example calcium, magnesium and sodium ions and salts thereof or may be deposits of water-carried soils, or even remnants from the cleaning product. During the course of this work, it has been observed that this problem can be exacerbated by some cleaning compositions which modify the surface of the dishware during the automatic dishwashing process such that after rinsing, discrete droplets or beads of water remain on the surface instead of draining off. These droplets or beads dry to leave noticeable spots or marks known as water-marks. This problem is particularly apparent on ceramic, stainless steel, plastic, glass and painted surfaces. The problem is more acute when the water used in the automatic dishwasher is hard water.

The object of the present invention is to provide an automatic dishwashing method that leaves the washed dishware shiny and with reduced incidence or free of spots.

SUMMARY OF THE INVENTION

According to the first aspect of the invention, there is provided a method of cleaning a soiled dishware load in an automatic dishwashing machine. The method comprises the step of subjecting the load to a wash liquor. The wash liquor comprises at least 700 ppm of an aminocarboxylated complexing agent. The liquor is free of phosphate and free of dispersant polymer. Preferably free of sulfonated polymer and free of carboxylated polymers, such as acrylates. Preferably the aminocarboxylated complexing agent is a salt of methyl glycine diacetic acid.

Dispersant polymers and in particular sulfonated polymers are widely accepted as part of phosphate-free automatic dishwashing compositions (see for example US 2010/0041575 A1). It has now been surprisingly found that the phosphate-free wash liquor of the invention performs better, in particular in terms of spotting prevention than wash liquors comprising dispersant polymers.

According to the second aspect of the invention, there is provided an automatic dishwashing cleaning composition. The composition comprises at least 25%, preferably at least 30% by weight of the composition of an aminocarboxylated complexing agent. Preferably the aminocarboxylated complexing agent is a salt of methyl glycine diacetic acid. The composition is free of phosphate and free of dispersant polymer.

According to the third aspect of the invention, there is provided a method of dishwashing, using the composition of the invention. Dishware cleaned according to the method of the invention is left with a reduced number of spots and very shiny even if the method is performed with hard water.

According to the last aspect of the invention, there is provided the use of the composition of the invention to reduce spotting in automatic dishwashing.

The elements of the method of the invention described in connection with the first aspect of the invention apply mutatis mutandis to the other aspects of the invention.

DETAILED DESCRIPTION OF THE INVENTION

The present invention encompasses a method of cleaning a soiled dishware load in an automatic dishwashing machine. The soiled dishware is contacted with a wash liquor. The wash liquor comprises at least 700 ppm, preferably at least 800 ppm, more preferably at least 900 ppm of an aminocarboxylated complexing agent. The wash liquour is free of phosphate and dispersant polymer, in particular free of sulfonated polymers and free of carboxylated polymers. The method leaves the dishware with a reduced number or free of spots even when the automatic dishwashing method is performed with hard water (i.e. water having more than 100, preferably 120 and especially more than 140 mg hardness ions/L). The invention also encompasses a phosphate-free automatic dishwashing cleaning composition. The composition comprises at least 25%, preferably at least 30% by weight of the composition of an aminocarboxylated complexing agent. The composition of the invention is free of dispersant polymer, preferably free of sulfonated polymers and free of carboxylated polymers. The composition has a good environmental profile, greatly reduces spotting and provides excellent cleaning and shine. The invention also encompasses the use of the composition to reduce spotting in automatic dishwashing.

For the purpose of this invention "dishware" encompasses tableware, cookware and any food-holding/handling items used for meal preparation, cooking and/or eating. Dishware is usually made of ceramic, stainless steel, plastic or glass.

By "dispersant polymer" is herein understood a polymer having a calcium binding capacity within the range between 30 to 250 mg of Ca/g of dispersant polymer, preferably between 35 to 200 mg of Ca/g of dispersant polymer, more preferably 40 to 150 mg of Ca/g of dispersant polymer at 25° C. In order to determine if a polymer is a dispersant polymer within the meaning of the invention, the following calcium binding-capacity determination is conducted in accordance with the following instructions:

Calcium Binding Capacity Test Method

The calcium binding capacity referred to herein is determined via titration using a pH/ion meter, such as the Meettler Toledo SevenMulti™ bench top meter and a PerfectION™ comb Ca combination electrode. To measure the binding capacity a heating and stirring device suitable for beakers or tergotometer pots is set to 25° C., and the ion electrode with meter are calibrated according to the manufacturer's instructions. The standard concentrations for the electrode calibration should bracket the test concentration and should be measured at 25° C. A stock solution of 1000 mg/g of Ca is prepared by adding 3.67 g of CaCl2-2H2O into 1 L of deionised water, then dilutions are carried out to prepare three working solutions of 100 mL each, respectively comprising 100 mg/g, 10 mg/g, and 1 mg/g concentrations of Calcium. The 100 mg Ca/g working solution is used as the initial concentration during the titration, which is conducted at 25° C. The ionic strength of each working solution is adjusted by adding 2.5 g/L of NaCl to each. The 100 mL of 100 mg Ca/g working solution is heated and stirred until it reaches 25° C. The initial reading of Calcium ion concentration is conducted at when the solution reaches 25° C. using the ion electrode. Then the test polymer is added incrementally to the calcium working solution (at 0.01 g/L intervals) and measured after 5 minutes of agitation following each incremental addition. The titration is stopped when the solution reaches 1 mg/g of Calcium. The titration procedure is repeated using the remaining two calcium concentration working solutions. The binding capacity of the test polymer is calculated as the linear slope of the calcium concentrations measured against the grams/L of test polymer that was added.

Dispersant polymers within the meaning of the invention are preferably selected from the group consisting of polymers having sulfonated monomers, polymers having carboxylated monomers and polymers having both sulfonated and carboxylated monomers.

The weight percent given herein is expressed as weight percentage of active material in the cleaning composition unless specified otherwise. The ppms are the ratio of 1 mg of active material per litre of water.

The automatic dishwashing cleaning composition of the invention can be in any physical form. It can be a loose powder, a gel or presented in unit dose form. The dosage for powders is typically from 15 to 30 grams, for gels from 15 to 40 ml and the weight of unit dose products is typically from 10 to 25 grams. Preferably it is in unit dose form, unit dose forms include pressed tablets and water-soluble packs. The automatic dishwashing cleaning composition of the invention is preferably presented in unit-dose form and it can be in any physical form including solid, liquid and gel form. The composition of the invention is very well suited to be presented in the form of a multi-compartment pack, more in particular a multi-compartment pack comprising compartments with compositions in different physical forms, for example a compartment comprising a composition in solid form and another compartment comprising a composition in liquid form. The composition is preferably enveloped by a water-soluble film such as polyvinyl alcohol. Especially preferred are compositions in unit dose form wrapped in a polyvinyl alcohol film having a thickness of less than 100 μm. The detergent composition of the invention weighs from about 8 to about 25 grams, preferably from about 10 to about 20 grams. This weight range fits comfortably in a dishwasher dispenser. Even though this range amounts to a low amount of detergent, the detergent has been formulated in a way that provides all the benefits mentioned herein above.

The liquor of the method of the invention is free of phosphate and free of dispersant polymer. By "liquor free" is meant that contains less than 20 ppm, preferably less than 10 ppm of the corresponding ingredient. By phosphate is meant sodium tripolyphosphate.

The composition is phosphate free. By "phosphate-free" is herein understood that the composition comprises less than 1%, preferably less than 0.1% by weight of the composition of phosphate. The composition is free of dispersant polymer. By "dispersant free" is herein understood that the composition comprises less than 1%, preferably less than 0.1% by weight of the composition of dispersant polymer.

The composition is preferably free of citric acid and salts thereof. By "free of citric acid and salts thereof" is herein understood that the composition comprises less than 1%, preferably less than 0.1% by weight of the composition of citric acid and salts thereof. Citric acid and salts thereof can cause discoloration of metal items, such as stainless steel in automatic dishwashing. Preferably, the composition is free of bicarbonate and silicate.

For the purpose of this invention a "complexing agent" is a compound capable of binding polyvalent ions such as calcium, magnesium, lead, copper, zinc, cadmium, mercury, manganese, iron, aluminium and other cationic polyvalent ions to form a water-soluble complex. The complexing agent has a logarithmic stability constant ([log K]) for $Ca^{2+}$ of at least 5, preferably at least 6. The stability constant, log K, is measured in a solution of ionic strength of 0.1, at a temperature of 25° C.

The liquor and the composition of the invention comprise an amino-carboxylated complexing agent, preferably selected from the group consisting of methyl-glycine-diacetic acid (MGDA), its salts and derivatives thereof, glutamic-N,N-diacetic acid (GLDA), its salts and derivatives thereof, iminodisuccinic acid (IDS), its salts and derivatives thereof, carboxy methyl inulin, its salts and derivatives thereof and mixtures thereof. Especially preferred complexing agent for use herein is selected from the group consisting of MGDA and salts thereof, especially preferred for use herein is the three sodium salt of MGDA.

The liquor of the method of the invention comprises more than 700, preferably more than 800 and especially more than 900 ppm of an aminocarboxylated complexing agent. Preferably less than 2000 ppm of an aminocarboxylated complexing agent.

The composition of the invention comprises at least 25% by weight of the composition of an aminocarboxylated complexing agent, preferably at least 30%. Preferably the composition comprises less than 60% by weight of the invention of an aminocarboxylated complexing agent.

Bleach

The liquor of the method of the invention preferably comprises from 100 to 1000 ppm, more preferably from 300 to 900 ppm of bleach.

The composition of the invention preferably comprises from about 1 to about 20%, more preferably from about 2 to about 15%, even more preferably from about 3 to about 12% and especially from about 4 to about 10% of bleach by weight of the composition.

Inorganic and organic bleaches are suitable for use herein. Inorganic bleaches include perhydrate salts such as perborate, percarbonate, perphosphate, persulfate and persilicate salts. The inorganic perhydrate salts are normally the alkali metal salts. The inorganic perhydrate salt may be included as the crystalline solid without additional protection. Alternatively, the salt can be coated. Suitable coatings include sodium sulphate, sodium carbonate, sodium silicate and mixtures thereof. Said coatings can be applied as a mixture applied to the surface or sequentially in layers.

Alkali metal percarbonates, particularly sodium percarbonate is the preferred bleach for use herein. The percarbonate is most preferably incorporated into the products in a coated form which provides in-product stability.

Potassium peroxymonopersulfate is another inorganic perhydrate salt of utility herein.

Typical organic bleaches are organic peroxyacids, especially dodecanediperoxoic acid, tetradecanediperoxoic acid, and hexadecanediperoxoic acid. Mono- and diperazelaic acid, mono- and diperbrassylic acid are also suitable herein. Diacyl and Tetraacylperoxides, for instance dibenzoyl peroxide and dilauroyl peroxide, are other organic peroxides that can be used in the context of this invention.

Further typical organic bleaches include the peroxyacids, particular examples being the alkylperoxy acids and the arylperoxy acids. Preferred representatives are (a) peroxybenzoic acid and its ring-substituted derivatives, such as alkylperoxybenzoic acids, but also peroxy-α-naphthoic acid and magnesium monoperphthalate, (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates, and (c) aliphatic and aralipathic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi (6-aminopercaproic acid).

Bleach Activators

Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from 1 to 12 carbon atoms, in particular from 2 to 10 carbon atoms, and/or optionally substituted perbenzoic acid. Suitable substances bear O-acyl and/or N-acyl groups of the number of carbon atoms specified and/or optionally substituted benzoyl groups. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), decanoyloxybenzoic acid (DOBA), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC). If present the composition of the invention comprises from 0.01 to 1, preferably from 0.2 to 0.5% by weight of the composition of bleach activator, preferably TAED. The liquor of the method of the invention preferably comprises from 1 to 100 ppm, more preferably from 20 to 80 ppm of bleach activator.

Bleach Catalyst

The composition herein preferably contains a bleach catalyst, preferably a metal containing bleach catalyst. More preferably the metal containing bleach catalyst is a transition metal containing bleach catalyst, especially a manganese or cobalt-containing bleach catalyst.

Bleach catalysts preferred for use herein include manganese triazacyclononane and related complexes; Co, Cu, Mn and Fe bispyridylamine and related complexes; and pentamine acetate cobalt(III) and related complexes.

Preferably the composition of the invention comprises from 0.001 to 0.5, more preferably from 0.002 to 0.05% of bleach catalyst by weight of the composition. Preferably the bleach catalyst is a manganese bleach catalyst. The liquor of the method of the invention preferably comprises from 0.05 to 1 ppm, more preferably from 0.1 to 0.05 ppm of bleach catalyst, preferably a manganese bleach catalyst.

Inorganic Builder

The composition of the invention preferably comprises an inorganic builder. Suitable inorganic builders are selected from the group consisting of carbonate, silicate and mixtures thereof. Especially preferred for use herein is sodium carbonate. Preferably the composition of the invention comprises from 5 to 50%, more preferably from 10 to 40% and especially from 15 to 30% of sodium carbonate by weight of the composition. The liquor of the method of the invention preferably comprises from 300 to 2000 ppm, more preferably from 500 to 1500 ppm of bleach catalyst. Preferably, the composition is free of silicate.

Surfactant

Surfactants suitable for use herein include non-ionic surfactants, preferably the compositions are free of any other surfactants. Traditionally, non-ionic surfactants have been used in automatic dishwashing for surface modification purposes in particular for sheeting to avoid filming and spotting and to improve shine. It has been found that non-ionic surfactants can also contribute to prevent redeposition of soils.

Preferably the composition of the invention comprises a non-ionic surfactant or a non-ionic surfactant system, more preferably the non-ionic surfactant or a non-ionic surfactant system has a phase inversion temperature, as measured at a concentration of 1% in distilled water, between 40 and 70° C., preferably between 45 and 65° C. By a "non-ionic surfactant system" is meant herein a mixture of two or more non-ionic surfactants. Preferred for use herein are non-ionic surfactant systems. They seem to have improved cleaning and finishing properties and better stability in product than single non-ionic surfactants.

Phase inversion temperature is the temperature below which a surfactant, or a mixture thereof, partitions preferentially into the water phase as oil-swollen micelles and above which it partitions preferentially into the oil phase as water swollen inverted micelles. Phase inversion temperature can be determined visually by identifying at which temperature cloudiness occurs.

The phase inversion temperature of a non-ionic surfactant or system can be determined as follows: a solution containing 1% of the corresponding surfactant or mixture by weight of the solution in distilled water is prepared. The solution is stirred gently before phase inversion temperature analysis to ensure that the process occurs in chemical equilibrium. The phase inversion temperature is taken in a thermostable bath by immersing the solutions in 75 mm sealed glass test tube. To ensure the absence of leakage, the test tube is weighed before and after phase inversion temperature measurement. The temperature is gradually increased at a rate of less than 1° C. per minute, until the temperature reaches a few degrees below the pre-estimated phase inversion temperature. Phase inversion temperature is determined visually at the first sign of turbidity.

Suitable nonionic surfactants include: i) ethoxylated nonionic surfactants prepared by the reaction of a monohydroxy alkanol or alkyphenol with 6 to 20 carbon atoms with preferably at least 12 moles particularly preferred at least 16 moles, and still more preferred at least 20 moles of ethylene oxide per mole of alcohol or alkylphenol; ii) alcohol alkoxylated surfactants having a from 6 to 20 carbon atoms and at least one ethoxy and propoxy group. Preferred for use herein are mixtures of surfactants i) and ii).

Another suitable non-ionic surfactants are epoxy-capped poly(oxyalkylated) alcohols represented by the formula:

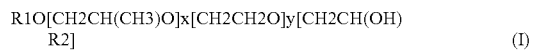

wherein R1 is a linear or branched, aliphatic hydrocarbon radical having from 4 to 18 carbon atoms; R2 is a linear or branched aliphatic hydrocarbon radical having from 2 to 26 carbon atoms; x is an integer having an average value of from 0.5 to 1.5, more preferably about 1; and y is an integer having a value of at least 15, more preferably at least 20.

Preferably, the surfactant of formula I, at least about 10 carbon atoms in the terminal epoxide unit [CH2CH(OH)R2]. Suitable surfactants of formula I, according to the present invention, are Olin Corporation's POLY-TERGENT® SLF-18B nonionic surfactants, as described, for example, in WO 94/22800, published Oct. 13, 1994 by Olin Corporation.

The composition of the invention preferably comprises from 1 to 10% by weight of the composition of surfactant, more preferably non-ionic surfactant.

The liquor of the method of the invention preferably comprises from 100 to 1000 ppm, more preferably from 200 to 600 ppm of surfactant, more preferably non-ionic surfactant.

Enzymes

In describing enzyme variants herein, the following nomenclature is used for ease of reference: Original amino acid(s):position(s):substituted amino acid(s). Standard enzyme IUPAC 1-letter codes for amino acids are used.

Proteases

Suitable proteases include metalloproteases and serine proteases, including neutral or alkaline microbial serine proteases, such as subtilisins (EC 3.4.21.62) as well as chemically or genetically modified mutants thereof. Suitable proteases include subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii*.

Especially preferred proteases for the detergent of the invention are polypeptides demonstrating at least 90%, preferably at least 95%, more preferably at least 98%, even more preferably at least 99% and especially 100% identity with the wild-type enzyme from *Bacillus lentus*, comprising mutations in one or more, preferably two or more and more preferably three or more of the following positions, using the BPN' numbering system and amino acid abbreviations as illustrated in WO00/37627, which is incorporated herein by reference: V68A, N87S, S99D, S99SD, S99A, S101G, S101M, S103A, V104N/I, G118V, G118R, S128L, P129Q, S130A, Y167A, R170S, A194P, V205I and/or M222S.

Most preferably the protease is selected from the group comprising the below mutations (BPN' numbering system) versus either the PB92 wild-type (SEQ ID NO:2 in WO 08/010925) or the subtilisin 309 wild-type (sequence as per PB92 backbone, except comprising a natural variation of N87S).

(i) G118V+S128L+P129Q+S130A
(ii) S101M+G118V+S128L+P129Q+S130A
(iii) N76D+N87R+G118R+S128L+P129Q+S130A+S188D+N248R
(iv) N76D+N87R+G118R+S128L+P129Q+S130A+S188D+V244R
(v) N76D+N87R+G118R+S128L+P129Q+S130A
(vi) V68A+N87S+S101G+V104N Suitable commercially available protease enzymes include those sold under the trade names Savinase®, Polarzyme®, Kannase®, Ovozyme®, Everlase® and Esperase® by Novozymes A/S (Denmark), those sold under the tradename Properase®, Purafect®, Purafect Prime®, Purafect Ox®, FN3®, FN4®, Excellase®, Ultimase® and Purafect OXP® by Genencor International, those sold under the tradename Opticlean® and Optimase® by Solvay Enzymes, those available from Henkel/Kemira, namely BLAP.

Preferred levels of protease in the product of the invention include from about 0.1 to about 10, more preferably from about 0.5 to about 7 and especially from about 1 to about 6 mg of active protease. The liquor of the method of the invention preferably comprises from 1 to 10 ppm, more preferably from 2 to 5 ppm of active protease.

Amylases

Preferred enzyme for use herein includes alpha-amylases, including those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) the variants described in U.S. Pat. No. 5,856,164 and WO99/23211, WO 96/23873, WO00/60060 and WO 06/002643, especially the variants with one or more substitutions in the following positions versus the AA560 enzyme listed as SEQ ID No. 12 in WO 06/002643:
9, 26, 30, 33, 82, 37, 106, 118, 128, 133, 149, 150, 160, 178, 182, 186, 193, 195, 202, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482, 484, preferably that also contain the deletions of D183* and G184*.

(b) variants exhibiting at least 95% identity with the wild-type enzyme from *Bacillus sp.* 707 (SEQ ID NO:7 in U.S. Pat. No. 6,093,562), especially those comprising one or more of the following mutations M202, M208,S255, R172, and/or M261. Preferably said amylase comprises one of M202L or M202T mutations.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, POWERASE®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). Amylases especially preferred for use herein include NATALASE®, STAINZYME®, STAINZYME PLUS®, POWERASE® and mixtures thereof.

Preferably, the product of the invention comprises at least 0.01 mg, preferably from about 0.05 to about 10, more preferably from about 0.1 to about 6, especially from about 0.2 to about 5 mg of active amylase. The liquor of the method of the invention preferably comprises from 0.1 to 10 ppm, more preferably from 0.3 to 2 ppm of active amylase.

Preferably, the protease and/or amylase of the product of the invention are in the form of granulates, the granulates comprise less than 29% of sodium sulfate by weight of the granulate or the sodium sulfate and the active enzyme (protease and/or amylase) are in a weight ratio of less than 4:1.

Crystal Growth Inhibitor

Crystal growth inhibitors are materials that can bind to calcium carbonate crystals and prevent further growth of species such as aragonite and calcite.

Especially preferred crystal growth inhibitor for use herein is HEDP (1-hydroxyethylidene 1,1-diphosphonic acid). Preferably, the composition of the invention comprises from 0.01 to 5%, more preferably from 0.05 to 3% and especially from 0.5 to 2% of a crystal growth inhibitor by weight of the product, preferably HEDP.

Metal Care Agents

Metal care agents may prevent or reduce the tarnishing, corrosion or oxidation of metals, including aluminium, stainless steel and non-ferrous metals, such as silver and copper. Preferably the composition of the invention comprises from 0.1 to 5%, more preferably from 0.2 to 4% and especially from 0.3 to 3% by weight of the product of a metal care agent, preferably the metal care agent is benzo triazole (BTA).

Glass Care Agents

Glass care agents protect the appearance of glass items during the dishwashing process. Preferably the composition of the invention comprises from 0.1 to 5%, more preferably from 0.2 to 4% and specially from 0.3 to 3% by weight of the composition of a metal care agent, preferably the glass care agent is a zinc containing material, specially hydrozincite.

The automatic dishwashing composition of the invention preferably has a pH as measured in 1% weight/volume aqueous solution in distilled water at 20° C. of from about 9 to about 12, more preferably from about 10 to less than about 11.5 and especially from about 10.5 to about 11.5. The wash liquor preferably has a pH at 20° C. of from about 9 to about 12, more preferably from about 10 to less than about 11.5 and especially from about 10.5 to about 11.5.

The automatic dishwashing composition of the invention preferably has a reserve alkalinity of from about 8 to about 14 g, more preferably from about 10 to about 14 g at a pH of 9.5 as measured in NaOH with 100 ml of product at 20° C.

"Reserve alkalinity", as used herein refers to, the ability of an automatic dishwashing composition to maintain an alkali pH in the presence of acid. This is relative to the ability of an automatic dishwashing composition to have sufficient alkali in reserve to deal with any added acid—coming from the water and/or the soils on the dishware—while maintaining the pH.

More specifically, it is defined as the grams of NaOH per 100 cc's, exceeding pH 9.5, in product. The reserve alkalinity for a solution is determined in the following manner A pH meter (for example An Orion Model 720A) with a Ag/AgCl electrode (for example an Orion sure flow Electrode model 9172BN) is standardized using pH 7 and pH 10 buffers. A 1% solution of the composition to be tested is prepared in distilled water. The weight of the sample is noted. The pH of the 1% solution is measured and the solution is titrated down to pH 9.5 using a solution of 0.2N HCL. The reserve alkalinity is calculated in the following fashion:

Reserve Alkalinity=% NaOH×Specific Gravity.

% NaOH=ml HCl×Normality of HCl×4'/Weight of Sample Aliquot Titrated

* Equivalent weight of NaOH in the % NaOH equation, derived from:

% NaOH=ml HCl×Normality of HCl×Equiv. Weight NaOH×100/1000×Weight of Sample Aliquot Titrated.

EXAMPLES

To demonstrate the benefit of the present invention, the following compositions were prepared. Compositions B and C, according to the invention, were free of polymers and composition A was a comparative reference outside the scope of the invention.

TABLE 1

Example automatic dishwashing detergent compositions

| Grams active of material per dose | A | B | C |
|---|---|---|---|
| Powder section | | | |
| Sodium carbonate | 3 8 | 3.8 | 3.8 |
| Sodium sulphate | 1.1 | 1.1 | 1.1 |
| MGDA | 3.3 | 4.3 | 4.7 |
| Polymer | 1.3 | — | — |
| Sodium percarbonate | 2.6 | 2.6 | 2.6 |
| Bleach activator | 0.2 | 0.2 | 0.2 |
| Nonionic surfactant 1 | 0.1 | 0.1 | 0.1 |
| Stainzyme Plus | 3 mg | 3 mg | 3 mg |
| Ultimase | 11 mg | 11 mg | 11 mg |
| HEDP | 0.1 | 0.1 | 0.1 |
| Liquid section | | | |
| Nonionic surfactant 1 | 0 6 | 0.6 | 0.6 |
| Nonionic surfactant 2 | 0.7 | 0.7 | 0.7 |
| Dipropylene glycol | 0.3 | 0.3 | 0.4 |
| Water soluble film | | | |
| PVA | 0.6 | 0.6 | 0.6 |

MGDA Trisodium salt of methylglycinediacetic acid, supplied by BASF
Polymer Sulphonated polymer Acusol 588 supplied by Dow Chemical
Bleach activator Tetraacetylethylenediamine
Stainzyme Plus Amylase supplied by Novozymes
Ultimase Protease supplied by DuPont
Nonionic surfactant 1 Plurafac SLF 180, supplied by BASF.
Nonionic surfactant 2 Lutensol T07, supplied by BASF.
HEDP 1-hydroxyethane 1,1-diphosphonic acid The compositions were used in an automatic dishwashing machine. The levels of MGDA in the wash liquor were: 660 ppm, 860 ppm and 940 ppm for compositions A, B and C, respectively.

Spotting Evaluation

To evaluate the anti-spotting benefit of the compositions, the number of spots left on tumbler-style glasses, and knives were counted after being washed five times with the compositions described herein before.

The glasses and knives were conditioned and washed five times in a dishwashing machine using a 55° C. normal cycle, with 50 g of ATS soil added at the beginning of each wash, using hard water (21 US gpg (144 mg hardness ions/L)). At the end of the five cycles the items were carefully assessed following the spotting test method described herein after.

TABLE 2

Spot count of glasses and knives after 5 cycles

| Glass | Glass Spot Count | Knife Spot Grade |
|---|---|---|
| Composition A | 89 | 6.6 |
| Composition B | 64 | 7.6 |
| Composition C | 14 | 9.3 |

As it can be seen from Table 2, the number of spots left on glasses washed with the detergents of the invention (Compositions B and C) is significantly smaller than those on glasses washed with a comparative detergent (Composition A). The spot grade on knives of composition B and C is higher than that of Composition A, indicating a significant improvement.

Filming Evaluation

To demonstrate that the inorganic filming prevention was maintained with the compositions of the inventions vs. the reference composition, in spite of the absence of polymer, a second multicycle test was run following the filming test method described herein after. The anti-filming performance was observed in glasses, plastic tumblers and stainless steel knives after fifteen wash cycles.

The glasses and knives were conditioned before the multicycle test and the plastic tumblers were washed as new. The glasses, plastic tumblers and knives were washed in a dishwashing machine using a 65° C. normal cycle, with 50 g of filming soil added at the beginning of each wash, using hard water (21 US gpg (144 mg hardness ions/L)). At the end of the fifteen wash cycles the items were carefully assessed following the filming test method described herein after.

TABLE 3

Glass and plastic clarity and knives color change after 15 cycles.

| Glass | Glass Clarity (%) | Plastic Clarity (%) | Knives Delta E |
|---|---|---|---|
| Composition A | 95.1 | 63.4 | 2.1 |
| Composition B | 93.1 | 64.1 | 2.1 |
| Composition C | 95.1 | 64.1 | 1.6 |

Table 3 shows that when items were washed 15 times with the compositions of the invention (Compositions B and C, without polymer), the anti-filming performance is overall maintained to the comparative composition including a polymer (Composition A).

Spotting Test Method

Four new stainless steel knives (such as Heaton Caterers knives) per composition were conditioned by hand-washing them using a sponge with 2 mL of a dishwashing liquid (Fairy dishwashing liquid) directly applied on the sponge and rinsed under running water, the knives and six new drinking glasses (such as Libbey® part number 158LIB Heavy Base 20 Oz. Ice Tea Glass Tumbler, from Libbey Inc, Toledo, Ohio, U.S.A.) were conditioned by washing them with a phosphate-free automatic dishwashing cleaning composition, (dishwashing cleaning composition specified herein as Composition A of table 1), then the glasses and knives were washed again with 20 g of food-grade citric acid powder. Both washes were carried out using a Miele GSL dishwashing machine (Miele Co. Ltd, Oxon, U.K.) in a normal wash 55° C. program, with soft water (3 US gpg, less than 21 ppm of $Ca^{2+}$ and $Mg^{2+}$ cations).

After being conditioned as described herein before, the glasses and knives were washed with the compositions of Table 1 by placing the six glasses on the top rack of the dishwasher, the four knives in the cutlery rack of the dishwasher, and placing one plastic pot containing 50 g of ATS frozen soil (as detailed herein below) into a Miele GSL dishwashing machine (Miele Co. Ltd, Oxon, U.K), at the start of the main wash, at the same time as the dishwashing detergent compositions. A normal wash 55° C. program is carried out with hard water (21 US gpg (144 mg hardness ions/L)). The wash is repeated five times.

The ATS frozen soil composition is prepared using the following ingredients and preparation instructions:

| Soil Ingredient | Weight | Tolerance |
|---|---|---|
| Potato Starch - (such as Tipiak Fecule) | 136 g | ±0.5 g |
| Wheat Flour - (such as Rochambeau Farine de ble) | 109.5 g | ±0.5 g |
| Vegetable oil (such as Asda) | 108 g | ±0.5 g |
| Margarine - (such as Stork) | 108 g | ±0.5 g |
| Lard - (such as Asda) | 108 g | ±0.5 g |
| Single Cream | 219 g | ±0.5 g |
| Baking Spread - (such as Asda Best for Baking) | 108 g | ±0.5 g |
| Contents of Large Chicken Eggs | 219 g | ±0.5 g |
| Whole Milk - (such as Asda Own) | 219 g | ±0.5 g |
| Ketchup - (such as Heinz) | 75 g | ±0.5 g |
| Mustard - (such as Amora, Moutarde de Dijon) | 100 g | ±0.5 g |
| Benzoic - (such as ex Fluka or equivalent) | 18.5 g | ±0.2 g |
| Hard Water (20 US gpg) | 918 g | ±1 g |
| Total | 2446 g | |

Soil Preparation

1. Weigh out the appropriate amounts of each ingredient as detailed above.
2. Add water to the potato starch, heat in a pan stirring continuously until a thick gel is formed. Leave the pan to cool at room temperature overnight.
3. Add the Ketchup and mustard to a bowl and mix vigorously using food blender (such as a Blixer Coupe 5VV at Speed 6)) until fully combined, approximately 1 minute.
4. Melt Margarine (1 min), lard (2 min) and baking spread (1 min) individually in a microwave (full power 750W) and allow to cool to room temperature (15 mins) then mix together vigorously.
5. Add Wheat Flour and Benzoic acid to a bowl and mix vigorously.
6. Break approximately 6 large eggs into a bowl and mix the egg contents vigorously (1 min).
7. Weigh out 219 g of the egg contents into a bowl. Add 219 g vegetable oil to the eggs and stir using a hand blender (1 min)
8. Mix the cream and milk in a bowl (1 min)
9. Add all of the ingredients together into a large container and mix vigorously for 10 mins using the food blender (such as Blixer Coupe 5VV at Speed 6)
10. Weigh out 50 g batches of this mixture into plastic pots and freeze at approximately −18° C.

At the end of the five washes, the glasses were then photographed against a black background and the images were analyzed using computer aided software to count spots on the glasses. A spot is defined as a circular cluster larger than 4 pixels with higher gray scale (4 units) versus the background. The knives were assessed according to a visual grading scale from 1-10, 10 being completely clean and 1 being extremely spotty. The visual grades are recorded by three individuals and averaged. A difference of 1.0 is classed as significant.

Filming Test Method

Four new stainless steel knives (such as Heaton Caterers knives) per composition were conditioned by hand-washing them using a sponge with 2 mL of a dishwashing liquid (Fairy dishwashing liquid) directly applied on the sponge and rinsed under running water, the knives and six new drinking glasses (such as Libbey® part number 158LIB Heavy Base 20 Oz. Ice Tea Glass Tumbler, from Libbey Inc, Toledo, Ohio, U.S.A.) were conditioned by washing them with a phosphate-free automatic dishwashing cleaning composition, (dishwashing cleaning composition specified herein as Composition A of Table 1), and then the glasses and knives were washed again with 20 g of food-grade citric acid powder. Both washes were carried out using a Miele GSL dishwashing machine (Miele Co. Ltd, Oxon, U.K.) or equivalent, in a normal wash 55° C. program, with soft water (3 US gpg, less than 21 ppm of $Ca^{2+}$ and $Mg^{2+}$ cations). The six plastic tumblers were added to the test without conditioning as new.

The four knives were the labelled and measured for their L*a*b values using a chroma-meter hand held device as explained herein after.

After being conditioned as described herein before, the glasses and knives were washed with the compositions of Table 1 by placing the twelve glasses (glass and plastic) on the top rack of the dishwasher, the four knives in the cutlery rack of the dishwasher, and placing one plastic pot containing 50 g of filming soil (as detailed herein below) into a Miele GSL dishwashing machine (Miele Co. Ltd, Oxon, U.K) at the start of the main wash, at the same time as the dishwashing detergents. A normal wash 65° C. program is carried out with hard water (21 US gpg (144 mg hardness ions/L)). The wash is repeated 15 times.

The filming soil composition is prepared using the following ingredients and preparation instructions:

| Ingredient | Weight | Tolerance |
| --- | --- | --- |
| Tap Water | 2500 g | ±1 g |
| Instant mashed potatoes - (such as Smash) | 18 g | ±0.2 g |
| Full fat UHT milk | 179 g | ±0.5 g |
| Tomato Ketchup - (such as Heinz) | 89 g | ±0.5 g |
| Mustard - (such as Coleman's English Mustard) | 89 g | ±0.5 g |
| Gravy granules - (such as Bisto Gravy) | 89 g | ±0.5 g |
| Margarine - (such as Stork) | 357 g | ±1 g |
| Egg Yolk | 179 g | ±1 g |
| Total | 3500 g | |

1. Weigh out the appropriate amounts of each ingredient as detailed above.
2. Add the water into a pan and heat to approximately 50° C.
3. Add all of the ingredients except the margarine to warm water stirring well to avoid the formation of lumps.
4. Cut the margarine into small pieces or slices of about 1 cm thickness.
5. Slowly add the margarine pieces into the warm mixture, stirringly continuously.
6. Increase the heat and bring the mixture to about 88-90° C., simmering. Then turn the heat down to the lowest setting and cook for 10 minutes.
7. Allow the mixture to cool to at least 35° C.,
8. Weight the mixture and top up with city water to 3500 g and stir well.
9. Weigh out 50 g batches of this mixture into plastic pots and freeze at approximately ~18 C After running 15 cycles, the glasses and plastic tumblers were then photographed against a black background and the images were analyzed using computer aided software to determine the amount of inorganic filming formed on their surfaces expressed as percent clarity.

Filming on a glass surface against a black background appears white, the higher the amount of filming on a surface the whiter the glass will appear in the photo. A gray scale of 0 to 255, where 0 is completely black and 255 is completely white is used and the Percent Clarity is a calculation of the gray level of the glass. A clarity index of 100 would occur with a completely dark glass with a gray level of zero. A clarity index of 0 would occur with a completely white glass with a gray level of 255.

The knives were analysed with a hand held chroma meter (such as Konica Minolta CR-400) for colour change. The colour is measured using XYZ tristimulus values which measure the wavelength and sensitivities. These values are then converted into the L*a*b colour space which consists of lightness variable L* and chromaticity indices a* and b*. The difference between the L*a*b values at the start of the 15 cycles and the end is calculated and is recorded as Delta E.

$$\Delta E = \sqrt{(L_i - L_f)^2 + (a_i - a_f)^2 + (b_i - b_f)^2}$$

Where $L_i$, $a_i$, and $b_i$, are the initial values and $L_f$, $a_f$ and $b_f$ are the values measured after 15 cycles. Delta E therefore measures the colour difference vs. clean items. The higher the number, the greater the colour change, which correlates to an item which has more inorganic filming. Typically a Delta E of less than three is not observed with the naked eye.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of cleaning a soiled dishware load in an automatic dishwashing machine comprising the step of subjecting the load to a wash liquor comprising at least 900 ppm of an aminocarboxylated complexing agent and wherein the liquor is free of phosphate and free of dispersant polymer and free of sulfonated polymer and free of carboxylated polymers, and wherein the wash liquour comprises a crystal growth inhibitor, wherein the complexing agent is selected from the group consisting of methyl glycine diacetic acid and its salts, wherein the wash liquor has a hardness greater than 140 mg hardness ions/L.

2. A method according to claim 1 wherein the wash liquor is free of citric acid and salts thereof.

3. A method according to claim 1 wherein the wash liquor further comprises an enzyme selected from amylase, protease and a mixture thereof.

4. A method according to claim 1 wherein the wash liquor comprises bleach and a bleach catalyst.

5. A method according to claim 1 wherein the wash liquor has a pH equal or greater than about 9 to about 12 at 20° C.

6. A method of reducing spotting on dishware during automatic dishwashing, the method comprising the step of subjecting the dishware to the wash liquor according to claim 1.

7. A phosphate-free automatic dishwashing cleaning composition comprising from 30% to 60% by weight of the composition of an aminocarboxylated complexing agent and wherein the composition is free of dispersant polymer, wherein the complexing agent is selected from the group consisting of methyl glycine diacetic acid and its salts, wherein the composition is in unit dose form.

8. A method of cleaning a soiled dishware load in an automatic dishwashing machine comprising the step of subjecting the load to a wash liquor comprising a composition according to claim 7.

9. A method of cleaning a soiled dishware load in an automatic dishwashing machine comprising the step of subjecting the load to a wash liquor comprising a composition according to claim 7 wherein the wash liquor comprises at least 700 ppm, of the aminocarboxylated complexing agent.

10. A method of cleaning a soiled dishware load in an automatic dishwashing machine comprising the step of subjecting the load to a wash liquor comprising a composition according to claim 7 wherein the wash liquor comprises at least 800 ppm of the aminocarboxylated complexing agent.

* * * * *